United States Patent
Reichman et al.

(10) Patent No.: US 8,512,253 B2
(45) Date of Patent: Aug. 20, 2013

(54) CEREBRAL PERFUSION MONITOR

(75) Inventors: Yosef Reichman, Kfar-Saba (IL); Ben Zion Poupko, Nes Ziona (IL); Shlomi Ben-Ari, Binyamina (IL)

(73) Assignee: Orsan Medical Technologies, Ltd (IL)

( * ) Notice: Subject to any disclaimer, the term of this patent is extended or adjusted under 35 U.S.C. 154(b) by 1525 days.

(21) Appl. No.: 11/921,937

(22) PCT Filed: Jan. 17, 2006

(86) PCT No.: PCT/IB2006/050174
§ 371 (c)(1),
(2), (4) Date: Dec. 11, 2007

(87) PCT Pub. No.: WO2006/134501
PCT Pub. Date: Dec. 21, 2006

(65) Prior Publication Data
US 2009/0227881 A1    Sep. 10, 2009

Related U.S. Application Data

(63) Continuation-in-part of application No. PCT/IL2005/000631, filed on Jun. 15, 2005, and a continuation-in-part of application No. PCT/IL2005/000632, filed on Jun. 15, 2005, each which is a continuation-in-part of application No. 10/893,570, filed on Jul. 15, 2004, now Pat. No. 7,998,080, which is a continuation-in-part of application No. PCT/IL03/00042, filed on Jan. 15, 2003.

(60) Provisional application No. 60/348,278, filed on Jan. 15, 2002.

(51) Int. Cl.
*A61B 5/02* (2006.01)
*A61B 5/05* (2006.01)

(52) U.S. Cl.
USPC ............................. 600/504; 600/506; 600/547

(58) Field of Classification Search
USPC .................. 600/300–301, 481–504, 506, 547
See application file for complete search history.

(56) References Cited

U.S. PATENT DOCUMENTS 3,994,284 A * 11/1976 Voelker ........................ 600/506
4,308,873 A    1/1982 Maynard
(Continued)

FOREIGN PATENT DOCUMENTS

EP    0314088    5/1989
EP    1057498    12/2000
(Continued)

OTHER PUBLICATIONS

Jevning, et al. "Evaluation of consistency among different electrical impedance indices of relative cerebral blood flow in normal resting individuals." Journal of Biomedical Engineering. vol. 11. Jan. 1989. pp. 53-56.*

(Continued)

*Primary Examiner* — Patricia Mallari
*Assistant Examiner* — Tiffany Weston
(74) *Attorney, Agent, or Firm* — Finnegan, Henderson, Farabow, Garrett & Dunner, LLP

(57) ABSTRACT

A method of estimating cerebral blood flow by analyzing IPG and PPG signals of the head, the method comprising:
  a) finding a maximum slope or most negative slope or the IPG signal, within at least a portion of the cardiac cycle;
  b) finding a maximum slope or most negative slope of the PPG signal, within at least a portion of the cardiac cycle;
  c) finding a ratio of the maximum or most negative slope of the IPG signal to the maximum or most negative slope of the PPG signal; and
  d) calculating a cerebral blood flow indicator from the ratio.

20 Claims, 9 Drawing Sheets

(56) References Cited

U.S. PATENT DOCUMENTS

| | | | |
|---|---|---|---|
| 4,649,932 | A | 3/1987 | Smith |
| 4,984,567 | A | 1/1991 | Kageyama et al. |
| 5,040,540 | A | 8/1991 | Sackner |
| 5,068,619 | A | 11/1991 | Nakano et al. |
| 5,265,615 | A | 11/1993 | Frank et al. |
| 5,282,840 | A | 2/1994 | Hudrlik |
| 5,315,512 | A * | 5/1994 | Roth .............................. 600/442 |
| 5,353,802 | A | 10/1994 | Ollmar et al. |
| 5,396,893 | A | 3/1995 | Oberg et al. |
| 5,694,939 | A | 12/1997 | Cowings |
| 5,746,214 | A | 5/1998 | Brown et al. |
| 5,749,369 | A | 5/1998 | Rabinovich et al. |
| 5,788,643 | A | 8/1998 | Feldman |
| 6,091,977 | A | 7/2000 | Tarjan et al. |
| 6,117,089 | A | 9/2000 | Sinha |
| 6,169,914 | B1 | 1/2001 | Hovland et al. |
| 6,223,069 | B1 | 4/2001 | Pfeiffer et al. |
| 6,245,027 | B1 | 6/2001 | Alperin |
| 6,413,223 | B1 | 7/2002 | Yang et al. |
| 6,491,647 | B1 | 12/2002 | Bridger et al. |
| 6,773,407 | B2 | 8/2004 | Yost et al. |
| 6,819,950 | B2 | 11/2004 | Mills |
| 6,832,113 | B2 | 12/2004 | Belalcazar |
| 6,875,176 | B2 | 4/2005 | Mourad et al. |
| 6,976,963 | B2 | 12/2005 | Clift |
| 6,996,428 | B2 | 2/2006 | Kislov et al. |
| 7,041,063 | B2 | 5/2006 | Abreu |
| 2004/0010185 | A1 | 1/2004 | Kimball et al. |
| 2004/0030258 | A1 | 2/2004 | Williams et al. |
| 2004/0034294 | A1 | 2/2004 | Kimball et al. |
| 2004/0049105 | A1 | 3/2004 | Crutchfield et al. |
| 2005/0054939 | A1 | 3/2005 | Ben-Ari et al. |
| 2006/0094964 | A1 | 5/2006 | Ragauskas et al. |
| 2006/0122523 | A1 | 6/2006 | Bonmassar et al. |
| 2006/0200033 | A1 | 9/2006 | Keren et al. |
| 2007/0287899 | A1 | 12/2007 | Poupko et al. |
| 2008/0004904 | A1 | 1/2008 | Tran |
| 2008/0021332 | A1 | 1/2008 | Brainard, III |
| 2008/0200787 | A1 | 8/2008 | Shapira et al. |
| 2008/0275352 | A1 | 11/2008 | Shapira et al. |

FOREIGN PATENT DOCUMENTS

| | | |
|---|---|---|
| GB | 1538695 | 1/1979 |
| JP | 03-118038 | 5/1991 |
| JP | 06-078888 | 3/1994 |
| JP | 2000-325324 | 11/2000 |
| JP | 2001-104274 | 4/2001 |
| JP | 2002-010986 | 1/2002 |
| JP | 2005-500116 | 1/2005 |
| RU | 2141249 | 11/1999 |
| WO | WO 96/16692 | 6/1996 |
| WO | WO 02/071923 | 9/2002 |
| WO | WO 02/087410 | 11/2002 |
| WO | WO 03/017834 | 3/2003 |
| WO | WO 03/059164 | 7/2003 |
| WO | WO 2006/006143 | 1/2006 |
| WO | WO 2006/011128 | 2/2006 |
| WO | WO 2006/087696 | 8/2006 |
| WO | WO 2006/134501 | 12/2006 |
| WO | WO 2008/072223 | 6/2008 |
| WO | WO 2010/041204 | 4/2010 |
| WO | WO 2010/041205 | 4/2010 |
| WO | WO 2010/041206 | 4/2010 |

OTHER PUBLICATIONS

Restriction Official Action Dated Dec. 13, 2011 From the US Patent and Trademark Office Re. U.S. Appl. No. 11/610,553.
Letter in Reponse Dated Dec. 7, 2010 to Telephone Conference With Examiner of Dec. 7, 2010 From the International Bureau of WIPO Re. Application No. PCT/IB2009/054392.
Letter in Reponse Dated Dec. 7, 2010 to Telephone Conference With Examiner of Dec. 7, 2010 From the International Bureau of WIPO Re. Application No. PCT/IB2009/054394.
Translation of Notificiation of Reasons for Rejection Dated Dec. 14, 2010 From the Japanese Patent Office Re. Application No. 2007-520969.
International Preliminary Report on Patentability Dated Dec. 21, 2010 From the International Preliminary Examining Authority Re. Application No. PCT/IB2009/054392.
International Preliminary Report on Patentability Dated Dec. 27, 2010 From the International Preliminary Examining Authority Re.: Application No. PCT/IB2009/054394.
Response Dated Jan. 12, 2011 to Telephone Conference With Examiner of Jan. 12, 2011 From the International Bureau of WIPO Re. Application No. PCT/IB2009/054388.
International Preliminary Report on Patentability Dated Jan. 21, 2011 From the International Preliminary Examining Authority Re. Application No. PCT/IB2009/054388.
Moshkalenko et al. "Slow Rhythmic Oscillations With the Human Cranium: Phenomenology, Origin, and Informational Significance", Human Physiology, 27(2): 171-178, 2001. Translated From Fiziologiya Cheloveka, 27(2): 47-55, 2001.
Weindling et al. "Effect of Electrode Size on the contributions of Intracranial and Extracranial Blood Flow to the Cerebral Electrical Impedance Plethysmogram", Medical & Biological Engineering & Computing, 20: 545-549, Sep. 1982.
Notice of Allowance Dated Jan. 30, 2012 From the US Patent and Trademark Office Re. U.S. Appl. No. 11/572,141.
Official Action Dated Nov. 27, 2009 From the US Patent and Trademark Office Re.: U.S. Appl. No. 10/893,570.
Response Dated Jan. 20, 2011 to Official Action of Nov. 5, 2010 From the US Patent and Trademark Office Re.: U.S. Appl. No. 10/893,570.
Translation of Notification of Reasons for Rejection Dated Mar. 22, 2011 From the Japanese Patent Office Re. Application No. 2007-520968.
Notice of Allowance Dated Apr. 11, 2011 From the US Patent and Trademark Office Re.: U.S. Appl. No. 10/893,570.
International Preliminary Report on Patentability Dated Apr. 21, 2011 From the International Bureau of WIPO Re. Application No. PCT/IB2009/054388.
Response Dated Feb. 27, 2011 to Office Action of Aug. 12, 2010 From the State Intellectual Property Office of the People's Republic of China Re. Application No. 200780051314.2.
Translation of Office Action Dated Aug. 12, 2010 From the State Intellectual Property Office of the People's Republic of China Re. Application No. 200780051314.2.
Communication Pursuant to Article 94(3) EPC Dated Apr. 28, 2011 From the European Patent Office Re. Application No. 05752203.9.
International Search Report and the Written Opinion Dated Apr. 20, 2010 From the International Searching Authority Re.: Application No. PCT/IB2009/054388.
International Search Report and the Written Opinion Dated Apr. 20, 2010 From the International Searching Authority Re.: Application No. PCT/IB2009/054392.
Response Dated May 5, 2010 to Rejection Decision of Feb. 12, 2010 From the State Intellectual Property Office of the People's Republic of China Re.: Application No. 200580031089.7.
Lovett Doust et al. "Aspects of the Cerebral Circulation During Non-REM Sleep in Healthy Controls and Psychiatric Patients, as Shown by Rheoencephalography", Psychophysiology, XP002572590, 12(5): 493-498, 1975. Abstract, p. 494, r-h Col., § 2—p. 495, 1-h Col., § 5, p. 495, 1-h Col., § 1, p. 495, 1-h Col., § 5—r-h Col., § 1, p. 496, 1-h Col., Fig.1, Tables 1-2.
Communication Pursuant to Article 94(3) EPC Dated Apr. 3, 2009 From the European Patent Office Re.: Application No. 05750856.6.
Communication Pursuant to Article 94(3) EPC Dated Feb. 24, 2010 From the European Patent Office Re.: Application No. 07827394.3.
Communication Pursuant to Article 94(3) EPC Dated Mar. 29, 2010 From the European Patent Office Re.: Application No. 05750856.6.
Communication Relating to the Results of the Partial International Search Dated Dec. 28, 2009 From the International Searching Authority Re.: Application No. PCT/IB2009/054392.
Communication Relating to the Search of the Partial International Search Dated Dec. 29, 2009 From the International Searching Authority Re.: Application No. PCT/IB2009/054388.

International Search Report and the Written Opinion Dated Dec. 23, 2009 From the International Searching Authority Re.: Application No. PCT/IB2009/054394.
Rejection Decision Dated Feb. 12, 2010 From the State Intellectual Property Office of the People's Republic of China Re.: Application No. 200580031089.7 and Its Translation Into English.
Response Dated Mar. 1, 2010 to Official Action of Nov. 27, 2009 From the US Patent and Trademark Office Re.: U.S. Appl. No. 10/893,570.
Supplementary European Search Report Dated Jan. 28, 2010 From the European Patent Office Re.: Application No. 05752203.9.
Abboud et al. "Left-Right Asymmetry of Visual Evoked Potentials in Brain- Damaged Patients: A Mathematical Model and Experimental Results", Annals of Biomedical Engineering, XP000578781, 24(1): 75-86, Jan. 1, 1996. Abstract, Fig.1.
Barbosa-Silva et al. "Bioelectrical Impedance Analysis: Population Reference Values for Phase Angle by Age and Sex", The American Journal of Clinical Nutrition, 82: 49-52, 2005.
González et al. "A Theoretical Study on Magnetic Induction Frequency Dependence of Phase Shift in Oedema and Haematoma", Physiological Measurement, 27: 829-838, 2006.
Jacquy et al. "Cerebral Blood Flow and Quantitative Rheoencephalography", Electroencephalographyand Clinical Neurophysiology, 37: 507-511, 1974.
Jevning et al. "Evaluation of Consistency Among Different Electrical Impedance Indices of Relative Cerebral Blood Flow in Normal Resting Individuals", Journal of Biomedical Engineering, XP022444925, 11(1): 53-56, Jan. 1, 1989.
Keren et al. "Evaluation of an Noninvasive Continuous Cardiac Output Monitoring System Based on Thoracic Bioreactance", American Journal of Physiology: Heart Circulation Physiology, 293: H583-H589, 2007.
Seoane Martinez "Electrical Bioimpedance Cerebral Monitoring: Fundamental Steps Toward Clinical Applications", Thesis for the Degree of Doctor of Philosophy, Department of Signals and Systems, Division of Biomedical Engineering, Chalmers University of Technology, Göteborg, Sweden & School of Engineering, University College of Borås, Borås, Sweden, 153 P., 2007.
Steiner et al. "Continuous Monitoring of Cerebrovascular Pressure Reactivity Allows Determination of Optimal Cerebral Perfusion Pressure in Patients With Traumatic Brain Injury", Critical Care Medicine, 30(4): 733-738, Apr. 2002. Abstract.
Stiefel et al. "Reduced Mortality Rate in Patients With Severe Traumatic Brain Injury Treated With Brain Tissue Oxygen Monitoring", Journal of Neurosurgery, 103(5): 805-811, Nov. 2005.
Communication Under Rule 71(3) EPC Dated May 18, 2011 From the European Patent Office Re.: Application No. 05750856.6.
Official Action Dated Apr. 13, 2011 From the US Patent and Trademark Office Re. U.S. Appl. No. 11/572,141.
Czosnyka "Cerebral Perfusion in Head-Injured Patients: A Nonivasive Assessment Using Transcranial Doppler Ultrasonography", Journal of Neurosurgery, 88: 802-808, 1998.
Grönlund et al. "Transephalic Electrical Impedance Provides a Means for Quantifying Pulsatile Cerebral Blood Volume Changes Following Head-Up Tilt", Early Human Development, 47: 11-18, 1997.
Ragauskas et al. "Implement of Non-Invasive Brain Physiological Moniitoring Concepts", Medical Engineering & Physics 25: 667-678, 2003.
Traczewski et al. "The Role of Computerized Rheoencephalography in the Assessment of Normal Pressure Hydrocephalus",Journal of Neutrotrauma, 22 (7): 836-843, 2005.
Wintermark et al. "Comparatibe Overview of Brain Perfusion Imaging Techniques", Stroke, vol. 36e, p. 83-99, 2005.
Translation of Notification to Grant Patent Right for Invention Dated May 26, 2011 From the State Intellectual Property Office of the People's Republic of China Re. Application No. 200780051314.2.
Communication Pursuant to Article 94(3) EPC Dated Jun. 2, 2010 From the European Patent Office Re. Application No. 05752203.9.
Official Action Dated Jun. 1, 2010 From the US Patent and Trademark Office Re.: U.S. Appl. No. 10/893,570.
Communication Pursuant to Article 94(3) EPC Dated Jun. 22, 2011 From the European Patent Office Re.: Application No. 07827394.3.

Translation of Notice of Reason for Rejection Dated Jun. 17, 2011 From the Japanese Patent Office Re. Application No. 2008-516457.
Official Action Dated Jun. 7, 2011 From the US Patent and Trademark Office Re. U.S. Appl. No. 11/572,157.
Bartocci et al. "Cerebral Blood-Flow Monitor for Use in Neonatal Intensive Care Units", Computer Methods and Programs in Biomedicine, 59: 61-73, 1999.
Colditz et al. "Continuous Cerebral Electrical Impedance Monitoring in Sick Preterm Infants", European Journal of Pediatrics, 149: 428-431, 1990.
Linderholm et al. "Imicroelectrical Impedance Tomography for Biophysical Characterization of Thin Film Biomaterials", Transducer '03, The 12th International Conference on Solid State Sensors, Actuators and Microsystems, Boston, Jun. 8-12, 2003, p. 284-287, Jun. 2003.
Response Dated May 31, 2011 to Notification of Reasons for Rejection of Dec. 14, 2010 From the Japanese Patent Office Re. Application No. 2007-520969.
Response Dated Jul. 18, 2010 to Communication Pursuant to Article 94(3) EPC of Feb. 24, 2010 From the European Patent Office Re.: Application No. 07827394.3.
Response Dated Jul. 19, 2010 to Communication Pursuant to Article 94(3) EPC of Mar. 29, 2010 From the European Patent Office Re.: Application No. 05750856.6.
Bellner et al. "Transcranial Doppler Sonography Pulsatility Index (PI) Reflects Intracranial Pressure (ICP)", Surgical Neurology, 62(1): 45-51, Jul. 2004.
Response Dated Jul. 26, 2010 to the Written Opinion of Dec. 23, 2009 From the International Searching Authority Re.: Application No. PCT/IB2009/054394.
Decision of Rejection Dated Jul. 28, 2011 From the Japanese Patent Office Re. Application No. 2007-520969 and Its Translation Into English.
Response Dated Jul. 19, 2011 to Notification of Reasons for Rejection of Mar. 22, 2011 From the Japanese Patent Office Re. Application No. 2007-520968.
Response Dated Aug. 9, 2010 to the Written Opinion of Apr. 20, 2010 From the International Searching Authority Re.: Application No. PCT/IB2009/054392.
Response Dated Jul. 29, 2010 to the Written Opinion of Apr. 20, 2010 From the International Searching Authority Re.: Application No. PCT/IB2009/054388.
International Preliminary Report on Patentability Dated Jan. 3, 2008 From the International Bureau of WIPO Re.: Application No. PCT/IB2006/050174.
International Preliminary Report on Patentability Dated Nov. 15, 2006 From the International Preliminary Examining Authority Re.: Application No. PCT/IL2005/000631.
International Preliminary Report on Patentability Dated May 23, 2007 From the International Preliminary Examining Authority Re.: Application No. PCT/IL05/00632.
International Preliminary Report on Patentability Dated Mar. 26, 2009 From the International Preliminary Examining Authority Re.: Application No. PCT/IL2007/001421.
International Search Report Dated Oct. 14, 2003 From the International Searching Authority Re.: Application No. PCT/IL03/00042.
Official Action Dated Feb. 20, 2009 From the US Patent and Trademark Office Re.: U.S. Appl. No. 10/893,570.
Written Opinion Dated Dec. 5, 2005 From the International Searching Authority Re.: Application No. PCT/IL05/000632.
Written Opinion Dated Oct. 20, 2005 From the International Searching Authority Re.: Application No. PCT/IL2005/000631.
Invitation to Restrict or Pay Additional Fees Dated Aug. 24, 2010 From the International Preliminary Examining Authority Re. Application No. PCT/IB2009/054388.
Response Dated Sep. 1, 2010 to Official Action of Jun. 1, 2010 From the US Patent and Trademark Office Re.: U.S. Appl. No. 10/893,570.
Response Dated Sep. 5, 2011 to Notice of Reason for Rejection of Jun. 17, 2011 From the Japanese Patent Office Re. Application No. 2008-516457.
Translation of Office Action Dated Jun. 5, 2009 From the State Intellectual Property Office of the People's Republic of China Re.: Application No. 200680029920.X.

Translation of Office Action Dated Aug. 7, 2009 From the State Intellectual Property Office of the People's Republic of China Re.: Application No. 200580031089.7.
Response Dated Oct. 3, 2010 to Communication Pursuant to Article 94(3) EPC of Jun. 2, 2010 From the European Patent Office Re. Application No. 05752203.9.
Response Dated Oct. 11, 2011 to Official Action of Apr. 13, 2011 From the US Patent and Trademark Office Re. U.S. Appl. No. 11/572,141.
Response Dated Oct. 27, 2011 to Communication Pursuant to Article 94(3) EPC of Jun. 22, 2011 From the European Patent Office Re.: Application No. 07827394.3.
Response Dated Oct. 27, 2011 to Communication Pursuant to Article 94(3) EPC of Apr. 28, 2011 From the European Patent Office Re. Application No. 05752203.9.
Communication Relating to the Results of the Partial International Search Dated Dec. 29, 2009 From the International Searching Authority Re.: Application No. PCT/IB2009/054388.
International Search Report Dated Dec. 5, 2005 From the International Searching Authority Re.: Application No. PCT/IL05/00632.
International Search Report Dated Oct. 20, 2005 From the International Searching Authority Re.: Application No. PCT/IL2005/000631.
International Search Report Dated May 21, 2008 From the International Searching Authority Re.: Application No. PCT/IL2007/001421.
International Search Report Dated Jun. 23, 2006 From the International Searching Authority Re.: Application No. PCT/IB2006/050174.
Office Action Dated Sep. 5, 2008 From the Patent Office of the People's Republic of China Re.: Application No. 200580031088.2 and Its Translation Into English.
Office Action Dated May 23, 2008 From the Patent Office of the People's Republic of China Re.: Application No. 100580031089.7.
Official Action Dated Mar. 18, 2008 From the US Patent and Trademark Office Re.: U.S. Appl. No. 10/893,570.
Official Action Dated Sep. 19, 2008 From the US Patent and Trademark Office Re.: U.S. Appl. No. 10/893,570.
Written Opinion Dated May 21, 2008 From the International Searching Authority Re.: Application No. PCT/IL2007/001421.
Written Opinion Dated Jun. 23, 2006 From the International Searching Authority Re.: Application No. PCT/IB2006/050174.
Decision to Grant a European Patent Pursuant to Article 97(1) EPC Dated Nov. 10, 2011 From the European Patent Office Re.: Application No. 05752203.9.
Braunfels et al. "A Randomized, Controlled Trial of the Efficacy of Closed Chest Compressions in Ambulances", Preshop Emrge Care, 1(3): 128-131, 1997.
Gronlund.J. et al. "High Frequency Variability of Trancephalic Electrical Impedance. A New Parameter for Monitoring of Neonatal Cerebral Circulation?" The Annual International Confrrence of the Engineering in Medicine and Biology Society, 6: 2513-2515,1992.
Seipel et al. "Rheoencephalographic and Other Studies of Betahistine in Humans: I. The Cerebral and Peripheral Circulatory Effects of Single Doses in Normal Subjects", The Journal of Clinical Pharmacology, 15: 144-154, 1975.
Webster "Measurement of Flow and Volume of Blood", Medical Instrumentation: Appliccation and Design: 332-371, 1997.
Response Dated Nov. 7, 2011 to Official Action of Jun. 7, 2011 From the US Patent and Trademark Office Re. U.S. Appl. No. 11/572,157.
Response Dated Nov. 16, 2011 to Decision of Rejection of Jul. 28, 2011 From the Japanese Patent Office Re. Application No. 2007-520969.
Official Action Dated Nov. 5, 2010 From the US Patent and Trademark Office Re.: U.S. Appl. No. 10/893,570.

* cited by examiner

CEREBRAL PERFUSION MONITOR

RELATED APPLICATIONS

This Application is a National Phase of PCT Patent Application No. PCT/IB2006/050174 having International Filing Date of Jan. 17, 2006, which claims priority from, and is a continuation-in-part of two related PCT Patent Applications PCT/IL2005/000631 and PCT/IL2005/000632, both having International Filing Dates of Jun. 15, 2005, which are both continuations-in-part of U.S. patent application Ser. No. 10/893,570 filed on Jul. 15, 2004, which is a continuation-in-part of PCT Patent Application No. PCT/IL03/00042 having International Filing Date of Jan. 15, 2003, which claims benefit under 35 USC 119(e) from US Provisional Patent Application No. 60/348,278 filed on Jan. 15, 2002. The contents of the above Applications are all incorporated herein by reference.

FIELD OF THE INVENTION

The field of the invention relates to measuring blood flow in the head.

BACKGROUND OF THE INVENTION

There is a need to measure cerebral blood flow during various medical events and procedures, because any disturbance to the flow of blood to the brain may cause injury to the function of the brain cells, and even death of brain cells if the disturbance is prolonged. Maintaining blood flow to the brain is especially important because brain cells are more vulnerable to a lack of oxygen than other cells, and because brain cells usually cannot regenerate following an injury.

A number of common situations may cause a decrease in the general blood flow to the brain, including arrhythmia, myocardial infarction, and traumatic hemorrhagic shock. A sudden increase in blood flow to the brain may also cause severe damage, and is especially likely to occur in newborn or premature babies, although such an increase may also occur in other patients with certain medical conditions, or during surgery. In all these cases, data regarding the quantity of blood flow in the brain, and the changes in flow rate, may be important in evaluating the risk of injury to the brain tissue and the efficacy of treatment. The availability of such data may enable the timely performance of various medical procedures to increase, decrease, or stabilize the cerebral blood flow, and prevent permanent damage to the brain.

In the absence of a simple means for direct and continuous monitoring of cerebral blood flow, information about changes in cerebral blood flow is inferred indirectly by monitoring clinical parameters which can be easily measured, such as blood pressure. But due to the different relation between blood pressure and cerebral blood flow in different medical conditions, there may be situations in which cerebral blood flow is inadequate even when blood pressure appears to be adequate. Cerebral blood flow may also be inferred indirectly by monitoring neurological function, but since neurological dysfunction is often irreversible by the time it is detected, it is more desirable to detect changes in cerebral blood flow directly, while its effects on brain function are still reversible.

Existing means for measuring cerebral blood flow are complex, expensive, and in some cases invasive, which limits their usefulness. Three methods that are presently used only in research are 1) injecting radioactive xenon into the cervical carotid arteries and observing the radiation it emits as it spreads throughout the brain; 2) positron emission tomography, also based on the injection of radioactive material; and 3) magnetic resonance angiography, performed using a room-sized, expensive, magnetic resonance imaging system, and requiring several minutes to give results. These three methods can only be carried out in a hospital or other center that has the specialized equipment available, and even in a hospital setting it is not practical to monitor patients continuously using these methods.

A fourth method, trans-cranial Doppler (TCD) uses ultrasound, is not invasive and gives immediate results. However, TCD fails to give a correct determination of blood flow in about 15% of patients, due to the difficulty of passing sound waves through the cranium, and it requires great skill by professionals who have undergone prolonged training and practice in performing the test and deciphering the results. Another disadvantage of TCD is that it measures only regional blood flow in the brain, and does not measure global blood flow. Doppler ultrasound may also be used to measure blood flow in the carotid arteries, providing an estimate of blood flow to the head, but not specifically to the brain, and not including blood flow to the head through the vertebral arteries. Blood flow through the vertebral arteries is difficult to measure by ultrasound because of their proximity to the vertebrae.

Two additional techniques that are used, generally in research, to measure blood flow in the head and in other parts of the body are electric impedance plethysmography (IPG) and photoplethysmography (PPG). U.S. Pat. No. 6,819,950, to Mills, (disclosure of which is incorporated by reference) are describes the use of PPG to detect carotid stenosis, among other conditions. U.S. Pat. No. 5,694,939, to Cowings, (disclosure of which is incorporated by reference) describes biofeedback techniques for controlling blood pressure, which include the use of IPG in the lower leg and PPG in the finger. U.S. Pat. No. 5,396,893, to Oberg et al, (disclosure of which is incorporated by reference) states that PPG is superior to IPG for monitoring patients' cardiac and respiration rates. U.S. Pat. No. 6,832,113, to Belalcazar, (disclosure of which is incorporated by reference) describes the use of either IPG or PPG to measure blood flow, for purposes of optimizing a cardiac pacemaker. U.S. Pat. No. 6,169,914, to Hovland et al, (disclosure of which is incorporated by reference) describes the use of various types of sensors, including IPG and PPG, for monitoring female sexual arousal with a vaginal probe, and describes using different types of sensors in combination.

U.S. Pat. No. 6,413,223, to Yang et al, (disclosure of which is incorporated by reference) describes a probe, used on the finger, which contains two PPG sensors and one IPG sensor. The combined data from the three sensors, analyzed using a mathematical model of arterial blood flow, provides a more accurate measurement of blood flow than would be obtained by using IPG or PPG alone.

J. H. Seipel and J. E. Floam, in J. Clinical Pharmacology 15, 144-154 (1975) present the results of a clinical study of the effects of a drug, betahistidine, on cerebral, cranial, scalp and calf blood circulation. Rheoencephalography (REG), a form of IPG, was used to measure the amplitude of cerebral blood flow.

The disclosures of all of the above mentioned patents and publication are incorporated herein by reference.

SUMMARY OF THE INVENTION

An aspect of some embodiments of the invention relates to determining cerebral blood flow from IPG data, using the data only from selected cardiac cycles, and discarding the data from other cardiac cycles, according to characteristics of the IPG data and/or other data, for example EKG data. Optionally, the IPG data is obtained from electrodes placed on the head or in ears, for example as described in any of the above mentioned related patent applications. Optionally, the cerebral blood flow is determined from a combination of IPG data and PPG data, and characteristics of the IPG data, the PPG data, other data, or any combination of them, are used to select cardiac cycles from which the IPG and PPG data is used. Optionally, the PPG data is obtained from PPG sensors placed on the head or in the ears, for example as described in any of the above mentioned related patent applications. Optionally, these characteristics comprise the duration of the cardiac cycle, and data is used for cardiac cycles that have similar duration, while cardiac cycles with very different durations are discarded. Additionally or alternatively, the characteristics comprise a cross-correlation between the signal for each cardiac cycle and the following (or preceding) cardiac cycle, for the IPG signal and/or for the PPG signal. For example, data is used for a cardiac cycle only if the cross-correlation exceeds a threshold, for the IPG signal or for the PPG signal, or only if the cross-correlation exceeds a threshold for both the IPG and PPG signals.

As aspect of some embodiments of the invention relates to reducing breathing artifacts from IPG data and/or PPG data, before using the IPG data, or a combination of the IPG and PPG data, to measure cerebral blood flow. Breathing artifacts are reduced, for example, by adjusting the data differently in each cardiac cycle, such that the data at a particular phase in the cardiac cycle, or an average of the data over a particular range of phases of the cardiac cycle, always has a fixed value. Optionally, breathing artifacts are substantially removed from the IPG data and/or from the PPG data, for example the cerebral blood flow calculated from the IPG and PPG data varies by less than 10% as a function of phase of the breathing cycle, on average over many breathing cycles. Optionally, the particular phase in the cardiac cycle is the diastolic phase, as indicated, for example, by the peak of the R-wave, or as indicated by a minimum in the IPG signal or the PPG signal.

An aspect of some embodiments of the invention relates to using a ratio of a slope, optionally a maximum slope of the IPG signal to a slope, optionally a maximum slope of the PPG signal, as a measure of cerebral blood flow. This slope is believed to be strongly correlated with the blood inflow. Optionally, the maximum slope used for both the IPG and PPG signals is the maximum slope of the leading edge, following the diastolic phase. Alternatively, the maximum slope used for one or both signals is the slope of maximum absolute value at the trailing edge, preceding the diastolic phase. Optionally, the maximum slope is normalized, for example by dividing it by a measure of the amplitude of the signal for that cardiac cycle. Optionally, the resulting measurement of cerebral blood flow is then smoothed by using an average over time. For example, a running average over time is used, with a fixed time interval, for example a few seconds, or with a fixed number of cardiac cycles. Optionally, the smoothing is done over a time interval that varies with time, adapting to characteristics of the signal.

There is thus provided, in accordance with an exemplary embodiment of the invention, a method of estimating cerebral blood flow by analyzing IPG and PPG signals of the head, the method comprising:
a) finding a maximum slope or most negative slope or the IPG signal, within at least a portion of the cardiac cycle;
b) finding a maximum slope or most negative slope of the PPG signal, within at least a portion of the cardiac cycle;
c) finding a ratio of the maximum or most negative slope of the IPG signal to the maximum or most negative slope of the PPG signal; and
d) calculating a cerebral blood flow indicator from the ratio.

Optionally, finding the maximum or most negative slope comprises finding the maximum slope, for both the IPG and PPG signals, and finding a ratio comprises finding a ratio of the maximum slopes.

Optionally, the maximum slopes are maximums within a leading portion of the cardiac cycle.

Alternatively, finding the maximum or most negative slope comprises finding the most negative slope, for both the IPG and PPG signals, and finding a ratio comprises finding a ratio of the most negative slopes.

Optionally, the most negative slopes are most negative within a trailing portion of the cardiac cycle.

In an embodiment of the invention, the maximum or most negative slope of at least one of the signals is normalized to a measure of the amplitude of said signal.

Optionally, the measure of the amplitude is the peak-to-peak amplitude of said signal over the cardiac cycle.

Alternatively, the measure of the amplitude is an average value of said signal over the cardiac cycle.

Optionally, the PPG signal comes from a PPG sensor on the left side of the head.

Additionally or alternatively, the PPG signal comes from a PPG sensor on the right side of the head.

Additionally or alternatively, the PPG signal is an average of signals from a PPG sensor on the left side of the head and a PPG sensor on the right side of the head.

There is further provided, in accordance with an exemplary embodiment of the invention, a method of estimating time-varying cerebral blood flow, comprising:
a) obtaining a time-varying IPG signal of the head;
b) obtaining a time-varying PPG signal of the head;
c) using the IPG and PPG signals to calculate a time-varying indicator for cerebral blood flow; and
d) performing data processing on one or more of the IPG signal, the PPG signal, and the cerebral blood flow indicator, to reduce noise or artifacts or both.

In an embodiment of the invention, performing data processing comprises discarding data of the IPG signal, the PPG signal, or both, for cardiac cycles which meet one or more criteria for discarding.

Optionally, the criteria comprise having a duration outside an expected range.

Optionally, the expected range has a maximum between 1.3 and 2 times an average duration of cardiac cycles.

Additionally or alternatively, the criteria comprise one or both of the IPG signal and the PPG signal having a cross-correlation below a threshold, between that cardiac cycle and the following cardiac cycle.

Additionally or alternatively, the criteria comprise one or both of the IPG signal and the PPG signal having a cross-correlation below a threshold, between that cardiac cycle and the preceding cardiac cycle.

Optionally, the threshold is between +0.5 and +0.8.

In an embodiment of the invention, performing data processing comprises reducing breathing artifacts in the IPG signal, the PPG signal, or both.

Optionally, calculating the cerebral blood flow indicator comprises using the method according to an exemplary embodiment of the invention.

In an embodiment of the invention, performing data processing comprises smoothing the cerebral blood flow indicator.

Optionally, smoothing comprises finding an average over a time interval.

Optionally, smoothing comprises using a time scale that is adjusted adaptively, depending on behavior of the cerebral blood flow indicator as a function of time.

BRIEF DESCRIPTION OF THE DRAWINGS

Exemplary embodiments of the invention are described in the following sections with reference to the drawings. The drawings are not necessarily to scale and the same reference numbers are generally used for the same or related features that are shown on different drawings.

DETAILED DESCRIPTION OF EXEMPLARY EMBODIMENTS

Figure 1:
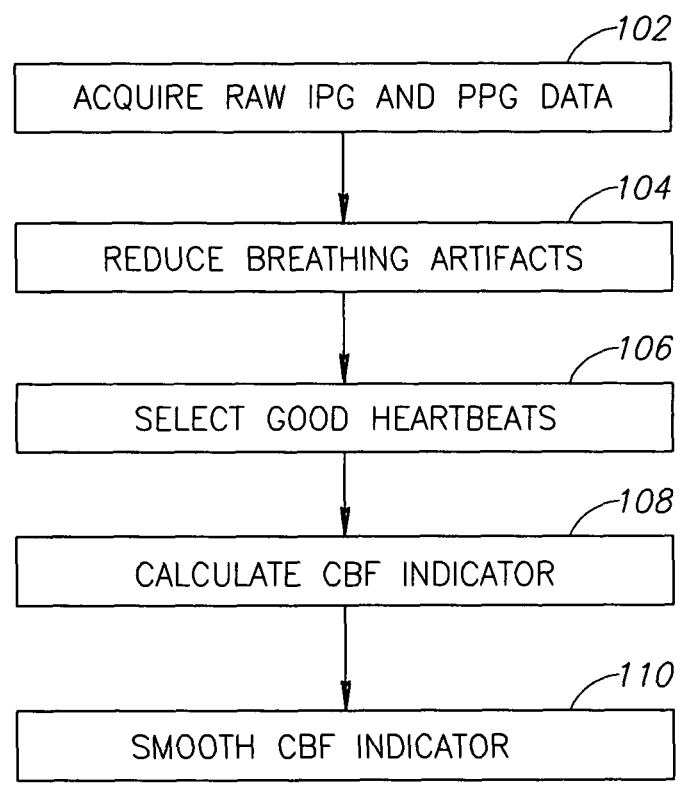
FIG. 1 is a flowchart of a method for finding cerebral blood flow, according to an exemplary embodiment of the invention.
Figure 2A:
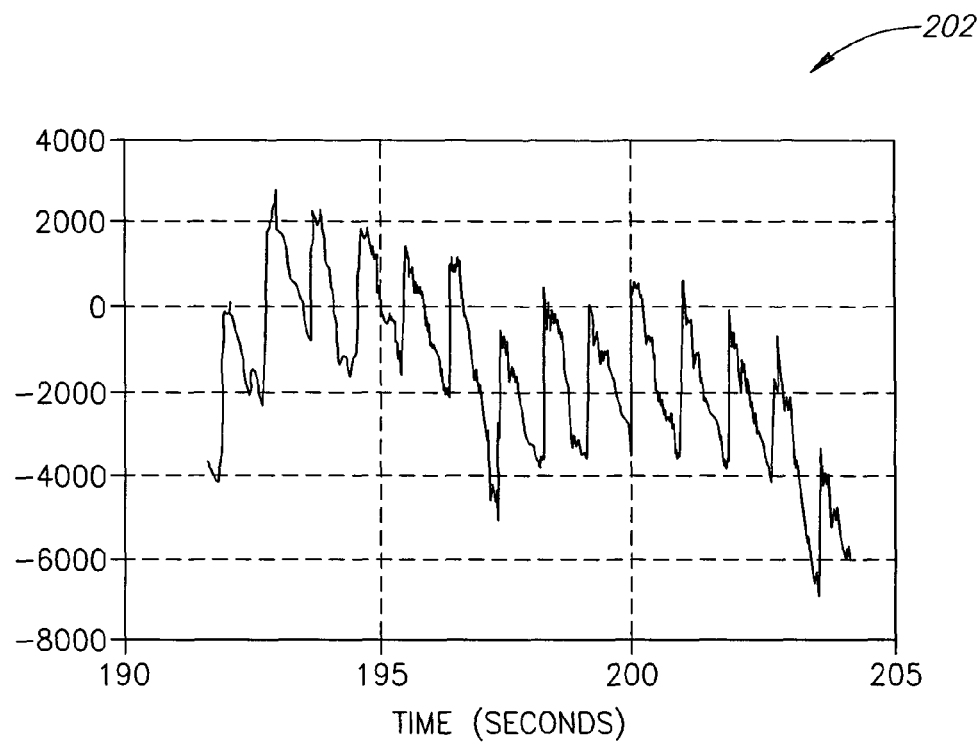
FIGS. 2A-2D schematically show graphs of IPG and PPG signals, with breathing artifacts and with the breathing artifacts removed, according to an exemplary embodiment of the invention.
Figure 2B:
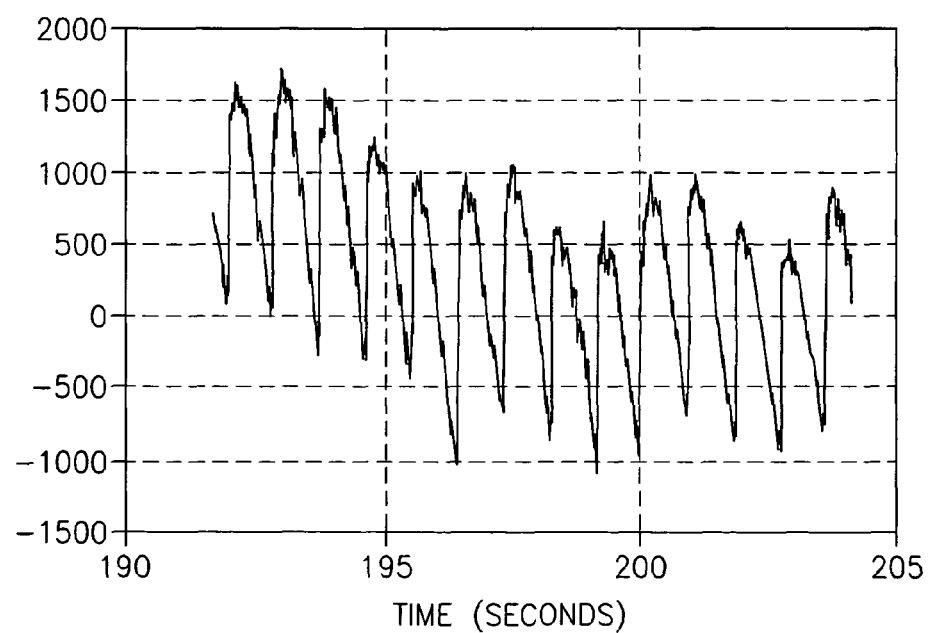
Figure 2C:
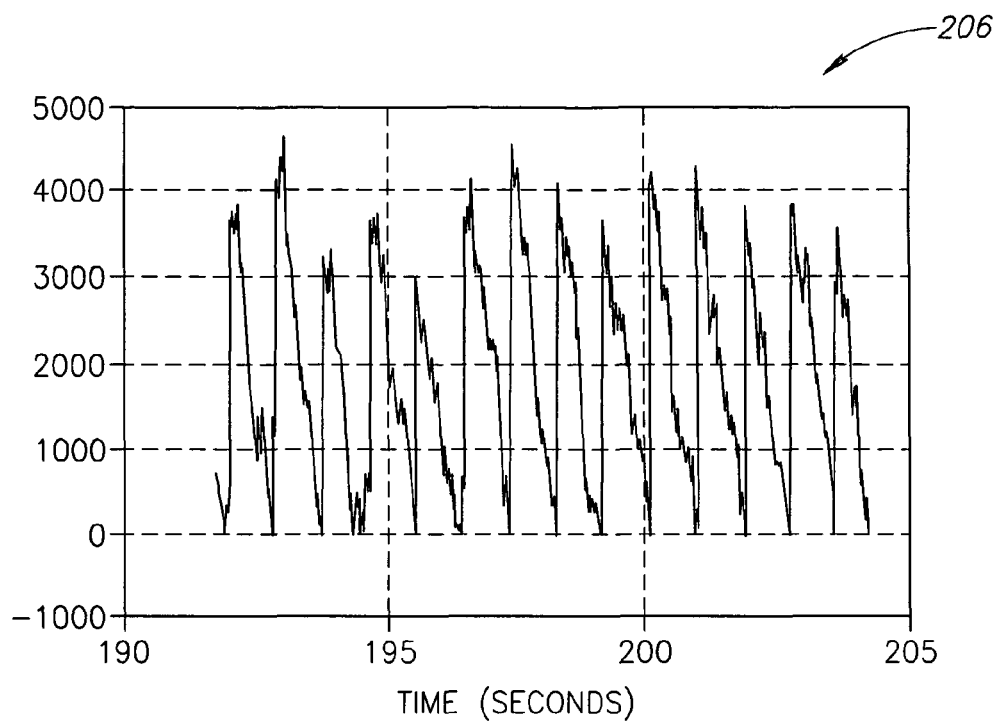
Figure 2D:
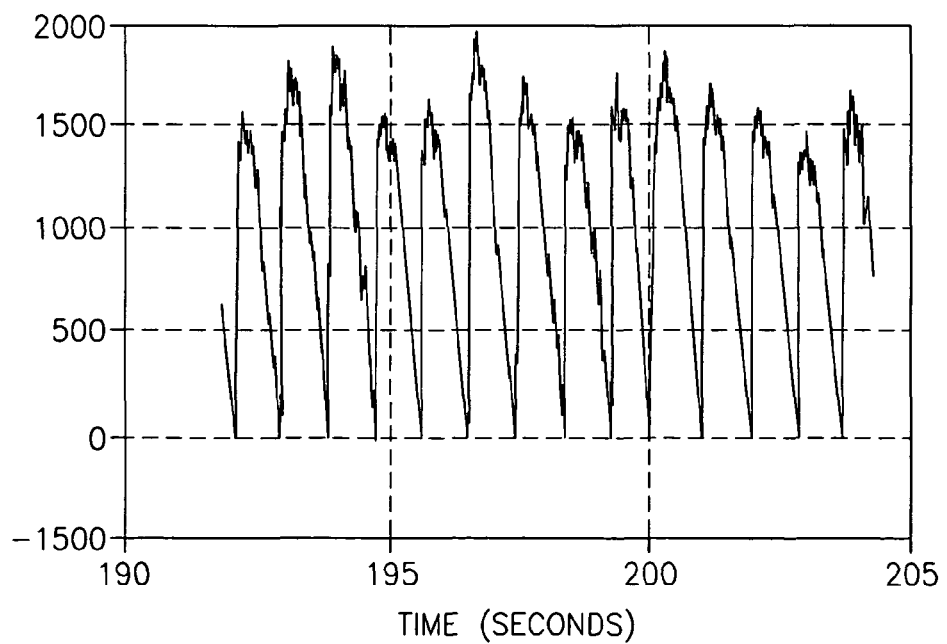

FIG. 1 shows a flowchart 100, outlining a method for finding cerebral blood flow (CBF) according to an exemplary embodiment of the invention. The different steps in flowchart 100 will be described with reference to graphs of data, shown in FIGS. 2, 3, and 4.

At 102, raw IPG and PPG data of the head is acquired. The data is acquired, for example, using any of the methods described in any of the above mentioned related patent applications or the patents, and publications as referenced in the Background, or any other methods known in the art for acquiring IPG and PPG data of the head. For example, combined sensors, incorporating both electrodes for IPG and optical sensors for PPG, are used, or separate sensors are used. Optionally, the IPG electrodes are designed to be of a size and shape, and are positioned on the head, so as to obtain IPG data that is relatively more sensitive to the impedance of the interior of the skull, and relatively less sensitive to the impedance of the scalp, as described in the above mentioned patent applications. Examples of raw IPG and PPG signals as a function of time are shown respectively in plots 202 and 204 of FIGS. 2A and 2B.

Optionally, there is more than one PPG sensor, for example, there are two PPG sensors, one on each side of the head. Optionally, the two PPG sensors are located respectively on the left and right sides of the forehead. In any of the methods described herein for using the PPG signal, either the PPG signal from the left side of the head or the PPG signal from the right side of the head may be used, or an average of the two PPG signals may be used, possibly a weighted average.

At 104, the raw IPG and/or PPG signals are optionally conditioned to reduce breathing artifacts. This is done, for example, by adjusting the signals so that the minimum value for each cardiac cycle has a constant value, set at zero in FIGS. 2C and 2D. Methods of defining what constitutes a single cardiac cycle are described below, in connection with 106. The resulting conditioned IPG signal, shown in plot 206, and conditioned PPG signal, shown in plot 208, are nearly free of breathing artifacts. There is no apparent correlation of the IPG signals and PPG signals with the breathing cycle visible to a casual viewer of plots 206 and 208, and any remaining correlation of the IPG signal and/or the PPG signal to the breathing cycle optionally results in less than a 10% effect on the calculated cerebral blood flow. Optionally, the values between minima are reduced by the average value or an interpolated value of the adjacent minima.

Optionally, at 106, "good" cardiac cycles are selected, and data from other cardiac cycles is discarded. Optionally, one or more of three criteria are used for discarding data from some cardiac cycles. The first criterion concerns how much the duration of the cardiac cycle differs from an average duration. The second and third criteria concern how much the form of the signal for a given cardiac cycle differs from the form of the signal for the following (or preceding) cardiac cycle, for the IPG signal and the PPG signal respectively. Data from cardiac cycles which satisfy one or more of these criteria is likely to have a high noise level which distorts the signals, or may correspond to an irregular heartbeat which does not provide a typical value for cerebral blood flow. The inventors have found that discarding data for cardiac cycles which satisfy any one of these three criteria is particularly useful for determining an accurate measure of cerebral blood flow. Optionally, data is discarded only if the cardiac cycle satisfies two of these criteria, or all three criteria. Optionally, only one of these three criteria is used as a criterion to discard data. Optionally, only two of the criteria are used, and the data is discarded if either of the two criteria is satisfied. Optionally, all three criteria are used, and the data is discarded if any of the criteria are satisfied. Other criteria for determining if the data for a particular cardiac cycle should be discarded will occur to a person of skill in the art.

The duration of the cardiac cycle is determined, for example, using EKG data, and defined as the time from the peak of one R-wave to the peak of the next R-wave. To be considered as the peak of an R-wave, the peak optionally must meet certain criteria. For example, the peak falls between 0.3 seconds and 1.5 seconds of the peak of the previous R-wave. If there is more than one local peak within this time interval, the peak of the R-wave is optionally found by finding the peak which most resembles the expected amplitude and time interval for the peak of an R-wave. The expected amplitude and time interval are based, for example, on the amplitude and time interval for the previous peak of an R-wave, or on a running average of past values. Optionally, instead of or in addition to using the peak of the R-wave to define the duration of the cardiac cycles, IPG data and/or PPG data is used. For example, the duration of a cardiac cycle is defined as the time from one local minimum (or maximum) to the next local minimum (or maximum) in the IPG and/or the PPG signal, or as the time from one local maximum (or minimum) in slope of the signal to the next local maximum (or minimum) in slope. Optionally, the local minimum or maximum in the IPG or PPG signal, or in the slope of the IPG or PPG signal, must meet certain criteria, for example criteria similar or identical to the criteria described above for using the peak of the R-wave. Optionally, data is discarded for those cardiac cycles that have a duration outside an expected range. Optionally, the maximum of the expected range is between 1.3 and 2 times an average duration of a cardiac cycle. For example, the maximum is 1.65 times the average duration. Alternatively, the maximum of the expected range is less than 1.3 times the average duration. Optionally, the minimum of the expected range is less than 0.7 times the average duration. Alternatively, the minimum of the expected range is more than 0.7 times the average duration. Optionally, there is no explicit minimum to the range, although there may be a minimum duration for any cardiac cycle, due to the way that cardiac cycles are defined, as described above.

The "average duration of a cardiac cycle" described above is optionally the median or the mode of the durations of the cardiac cycles. A potential advantage of using the median or the mode, rather than the mean, is that the median and the mode are relatively insensitive to the values of outliers that may represent noise in the data rather than real durations of cardiac cycles. Alternatively, the "average duration of a cardiac cycle" is the mean of the durations of cardiac cycles. Optionally, the "average duration of a cardiac cycle" is a running average, for example over several cardiac cycles, or over several tens of cardiac cycles. Using a running average for the average duration of a cardiac cycle has the potential advantage of adjusting the average duration to real changes in the patient's pulse rate, due to physiological changes over time. Optionally, a fixed value is used in place of the "average duration of a cardiac cycle," optionally adjusted to the patient, or the fixed value is based on a pulse rate determined for that patient.

How much the form of the signal (either the IPG or PPG signal) for a given cardiac cycle differs from the signal for the following cardiac cycle, is determined, for example, by the cross-correlation between the signals for the two cardiac cycles. Optionally, if the cross-correlation is less than some threshold, for one or both of the IPG and PPG signals, then the data for that cardiac cycle is discarded. Optionally, the threshold is between +0.5 and +0.8, for example the threshold is +0.7. Optionally, instead of using the cross-correlation between a cardiac cycle and the following cardiac cycle for the criterion, the criterion is based on the cross-correlation between the cardiac cycle and the previous cardiac cycle. Alternatively, the data is discarded only if either of these two cross-correlations is less than the threshold, or only if both cross-correlations are less than the threshold. Optionally, the data is discarded only if the cross-correlation (whichever one is used) is below the threshold for both the IPG and PPG signals. Alternatively, the data is discarded only if the cross-correlation is below the threshold for the IPG signal, or only if the cross-correlation is below the threshold for the PPG signal.

Figure 3:
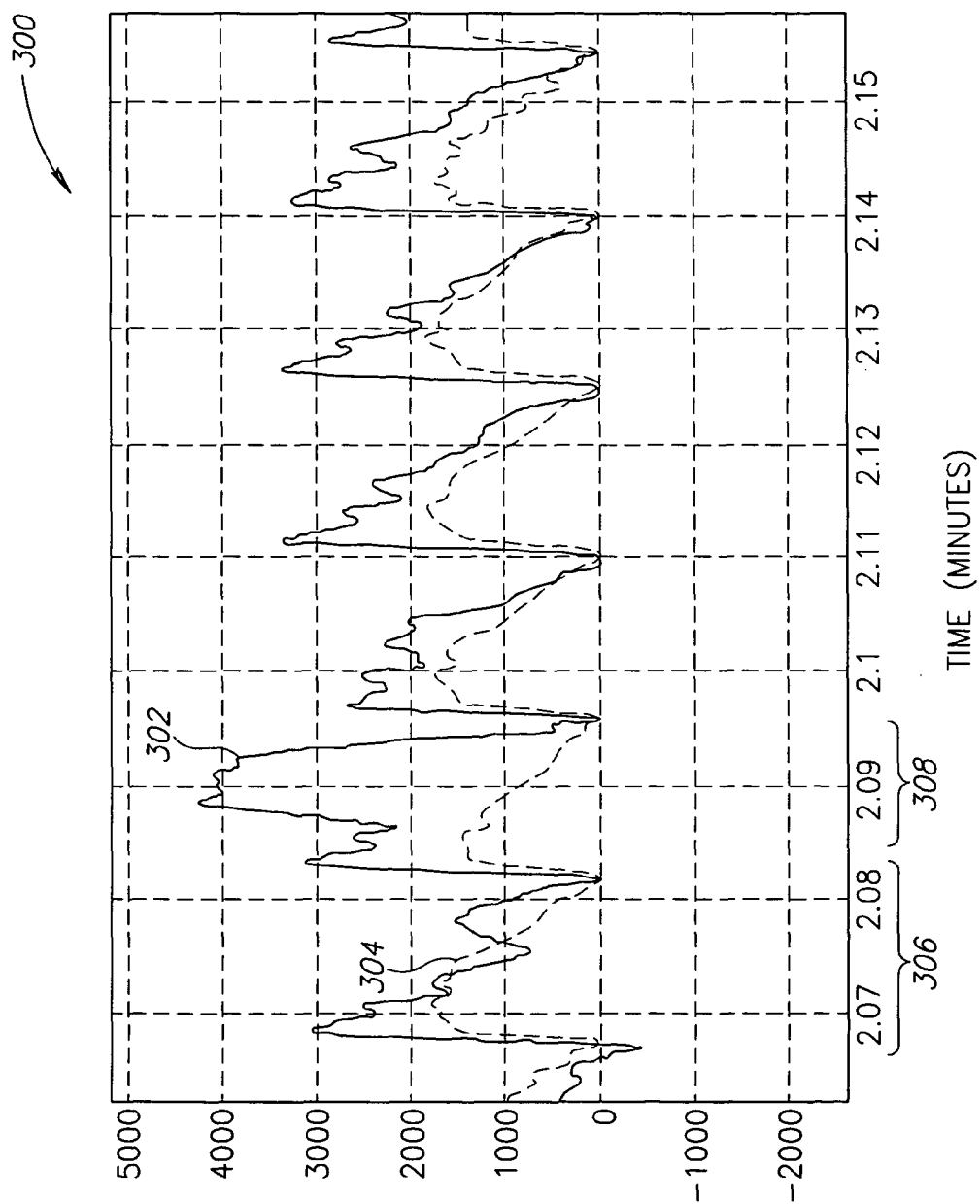
FIG. 3 schematically shows a graph of IPG and PPG signals, during good and bad cardiac cycles, according to an exemplary embodiment of the invention.

FIG. 3 shows a plot 300 of conditioned IPG data 302 (solid curve) and conditioned PPG data 304 (dashed curve). For the first two cardiac cycles, in time intervals 306 and 308, the cross-correlation between that cardiac cycle and the next is relatively low for the IPG data, apparently because of noise in the IPG data, and the data for these cardiac cycles is discarded. For the remaining cardiac cycles, the cross-correlation between that cardiac cycle and the next is relatively high, for both the IPG and the PPG signals, and the data for these cardiac cycles is not discarded.

At 108, a CBF indicator is calculated from the IPG and/or PPG data for the cardiac cycles for which the data has been kept. In an exemplary embodiment of the invention, the CBF indicator is found, for each such cardiac cycle, by taking the ratio of the maximum slope of the IPG signal to the maximum slope of the PPG signal. Optionally, the maximum slopes are not necessarily maximums over the whole cardiac cycle, but are maximums over a leading edge portion of the cardiac cycle, following the diastolic phase. It should be understood that the magnitudes of both the IPG and PPG signals, and hence the maximum slopes of both signals, in general may be sensitive to various factors. These factors include the exact position of the electrodes and PPG sensors on the patient's head, how good the contact is with the skin, and the thickness of the patient's skin and of the fatty layer beneath the patient's skin at the location of the electrodes and elsewhere on the patient's head. The ratio of the maximum slopes of the IPG and PPG signals may not provide an absolute measure of cerebral blood flow, but may provide only a relative measure of cerebral blood flow. Optionally, the measure of cerebral blood flow is calibrated by observing its value at a time when the patient is known to have adequate cerebral blood flow, for example before surgery, at a time when the patient is conscious and his mental state can be assessed by asking him questions. Optionally, the electrodes and PPG sensors are not removed or repositioned once the measure of cerebral blood flow has been calibrated, until surgery has been completed, for example.

Because the arteries in the brain are generally greater in diameter than the arteries of the skin of the face and the scalp, the blood volume in the brain generally increases sooner and faster at the beginning of the systolic phase, than the blood volume in the skin does. Because the IPG signal is sensitive both to the blood volume in the brain and the blood volume in the skin, while the PPG signal is sensitive only to the blood volume in the skin, the IPG signal generally rises sooner and faster, at the beginning of the systolic phase, than the PPG signal. The maximum slope of each signal is a measure of how fast this rise occurs, and how high the rise goes. The maximum slope of the IPG signal is a measure of a weighted sum of the blood flow in the brain and the blood flow in the skin, while the maximum slope of the PPG signal is a measure of the blood flow in the skin alone. The maximum slopes of the IPG and PPG signals may be better measures of blood flow in these regions than the peak-to-peak amplitude of the IPG and PPG signals, which measure changes in blood volume. The change in blood volume depends on the difference between blood flow into and out of a region. However, the peak-to-peak amplitudes of the IPG and PPG signals may also be useful for measuring cerebral blood flow.

Another useful measure of blood flow, for either the IPG signal or the PPG signal or both, is the maximum slope of the signal normalized to a measure of the amplitude of the signal. For example, the maximum slope is normalized by dividing by the peak-to-peak amplitude of the signal for that cardiac cycle. Alternatively, the maximum slope is normalized by dividing by a difference between an average value of the signal, possibly a weighted average value, and the minimum value of the signal, for that cardiac cycle. Optionally the weighted average value includes both positive and negative weights, for example the weighted average value is a Fourier component of the signal at the cardiac cycle frequency. Optionally, the normalization is to the area of the signal for example between successive minima.

The inventors have found that the ratio of maximum slope of the IPG signal to maximum slope of the PPG signal (either normalizing the maximum slopes or not) is often well correlated with blood flow rate in the brain in certain circumstances, as determined independently by other means, for example TCD. For example, in certain circumstances, the brain increases cerebral blood flow by constricting peripheral arteries which affect blood flow to the scalp and to the skin of the face. In these cases, an increase in cerebral blood flow correlates with a decrease in blood flow in the skin, and the ratio of maximum slope of IPG signal to maximum slope of PPG signal may be well correlated with cerebral blood flow.

In circumstances where cerebral blood flow is reduced by blocking or bleeding of an artery on one side of the head, the peripheral blood flow on the other side of the head may remain relatively constant. In these cases, particularly if the PPG signal is measured on the other side of the head from the affected artery, the ratio of the maximum slope of the IPG signal to the maximum slope of the PPG signal may also be well correlated with cerebral blood flow. Even if the PPG signal is taken on the same side of the head as the affected artery, the ratio of maximum slopes may be reasonably well correlated with cerebral blood flow, perhaps because collateral arteries may redistribute blood from one side of the head to the other.

In other circumstances, different measures of cerebral blood flow may be more useful. For example, if total blood flow to the head is reduced because of a decrease in blood pressure, then the brain may compensate by constricting peripheral arteries, reducing blood flow in the skin more than in the brain. In this case, the maximum slope of the IPG signal alone, or a weighted difference in maximum slopes between the IPG and PPG signals, may be a better measure of cerebral blood flow than the ratio of the maximum slopes.

In some embodiments of the invention, a different formula is used for finding the CBF indicator. For example, instead of using ratios of the maximum slopes of the IPG and PPG signals, the ratio of the minimum (most negative) slopes is used instead, with the slopes either normalized to a measure of the amplitudes or not. Optionally, the most negative slopes are not necessarily the most negative over the whole cardiac cycle, but only over a trailing edge portion of the cardiac cycle, following the systolic phase. The fall in blood volume after the systolic phase, like the rise in blood volume after the diastolic phase, may be faster for the brain than for the skin. The ratio of minimum slopes of the IPG and PPG signals may be related to cerebral blood flow in a similar way to the ratio of maximum slopes. Alternatively, when taking the ratio of slopes, the maximum slope is used for one of the signals and the minimum slope (or its absolute value) is used for the other signal.

Alternatively or additionally, the CBF indicator is found by subtracting a weighted PPG signal from the IPG signal, and then taking the maximum slope of the difference signal. Optionally, the weighting factor is determined by requiring a slope of the trailing edge of the weighted PPG signal, for example an average slope of the trailing edge, or a steepest slope of the trailing edge, to be equal to the corresponding slope of the IPG signal. This choice of weighting factor may be appropriate if the trailing edge of the IPG signal is dominated by blood flow in the skin. The resulting CBF indicator has the potential advantage that it may better indicate changes in cerebral blood flow caused by a decrease in blood pressure, which decreases blood flow in both the brain and the skin. On the other hand, a CBF indicator based on the ratios of the slopes of two signals may be less sensitive to noise in the signals than a CBF indicator based on the slope of a difference between two signals.

Optionally, the CBF indicator is based only on the IPG signal, or only on the PPG signal. For example, the CBF indicator is the peak-to-peak amplitude of one of the signals in each cardiac cycle, or the maximum or minimum slope of one of the signals, or the maximum or minimum slope normalized to an amplitude of the signal, in each cardiac cycle.

In 110, the CBF indicator signal is averaged over time, using any known algorithm for temporal smoothing. Optionally, the averaging is done over a time scale of several seconds, for example over 5, 10, or 20 seconds, or over a plurality of cardiac cycles, for example over 5, 10, or 20 cardiac cycles. Optionally, the time scale for the smoothing varies adaptively, depending on the data being smoothed. For example, the smoothing comprises averaging the data over a time interval which is adjusted upward if a linear extrapolation makes a good prediction about where the next data point will be, and is adjusted downward if a linear extrapolation makes a poor prediction about where the next data point will be.

Optionally, instead of, in addition to, averaging the CBF indicator over a plurality of cardiac cycles, the IPG signals for each of a plurality of cardiac cycles are superimposed and averaged together, and the same is optionally done for the PPG signal, before finding the CBF indicator in 108, using any of the methods described above.

Figure 4:
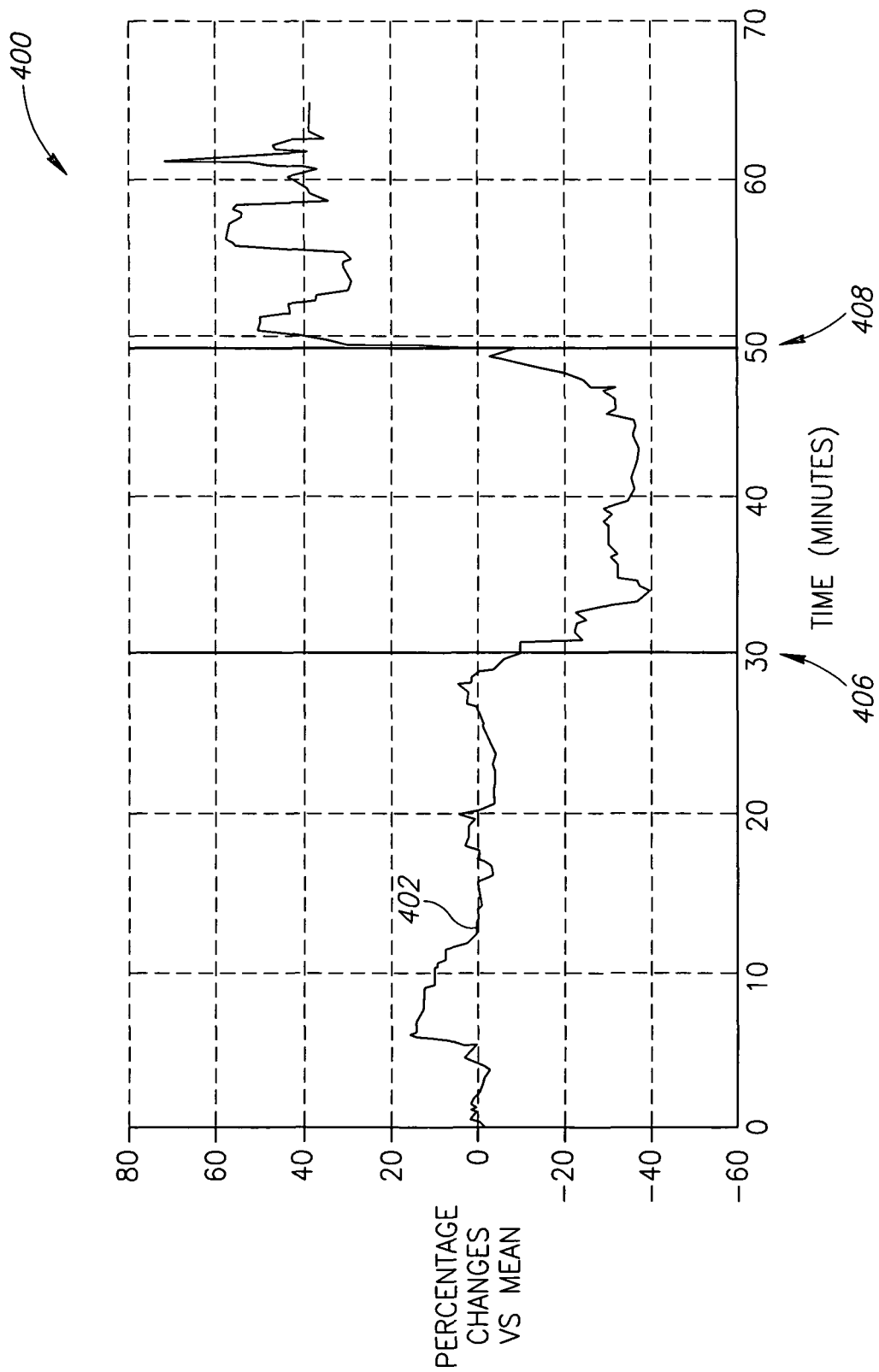
FIG. 4 schematically shows a graph of a calculated cerebral blood flow indicator as a function time during an endarterectomy procedure, according to an exemplary embodiment of the invention.

FIG. 4 shows a graph 400, with a plot of a smoothed CBF indicator signal 402 as a function of time. The CBF indicator was calculated by taking the ratio of the normalized maximum slope of the IPG signal to the normalized maximum slope of the PPG signal, with the normalization done using the peak-to-peak amplitude of each signal. The smoothing of the CBF indicator was done by averaging over an adaptively varying time interval, as described above. The IPG and PPG signals were measured on a patient undergoing an endarterectomy, in which the common, internal, and external carotid arteries on one side of the neck were clamped between time 406 and time 408, while the arteries were cleared of plaque. The PPG data used was taken from the side of the head opposite to the clamped arteries. The CBF indicator signal 402 decreases at time 406, primarily due to a decrease in the IPG signal, when the arteries are clamped and blood flow to that side of the head, and to the brain as a whole, is reduced. At time 408, when the clamped arteries are released, the CBF indicator signal 402 increases, primarily due to an increase in the IPG signal. The CBF indicator signal is higher after time 408 than it was before the arteries were clamped, because the arteries cleared of plaque allow greater cerebral blood flow than before.

It should be noted that this method of calculating the CBF indicator has been found by the inventors to generally give the best results for cerebral blood flow during an endarterectomy, of the methods that have been tested. However some other methods of calculating the CBF indicator, including using the PPG signal from the same side of the head as the clamped arteries, have also been found to give a fairly good indication of cerebral blood flow during endarterectomy.

Figure 5:
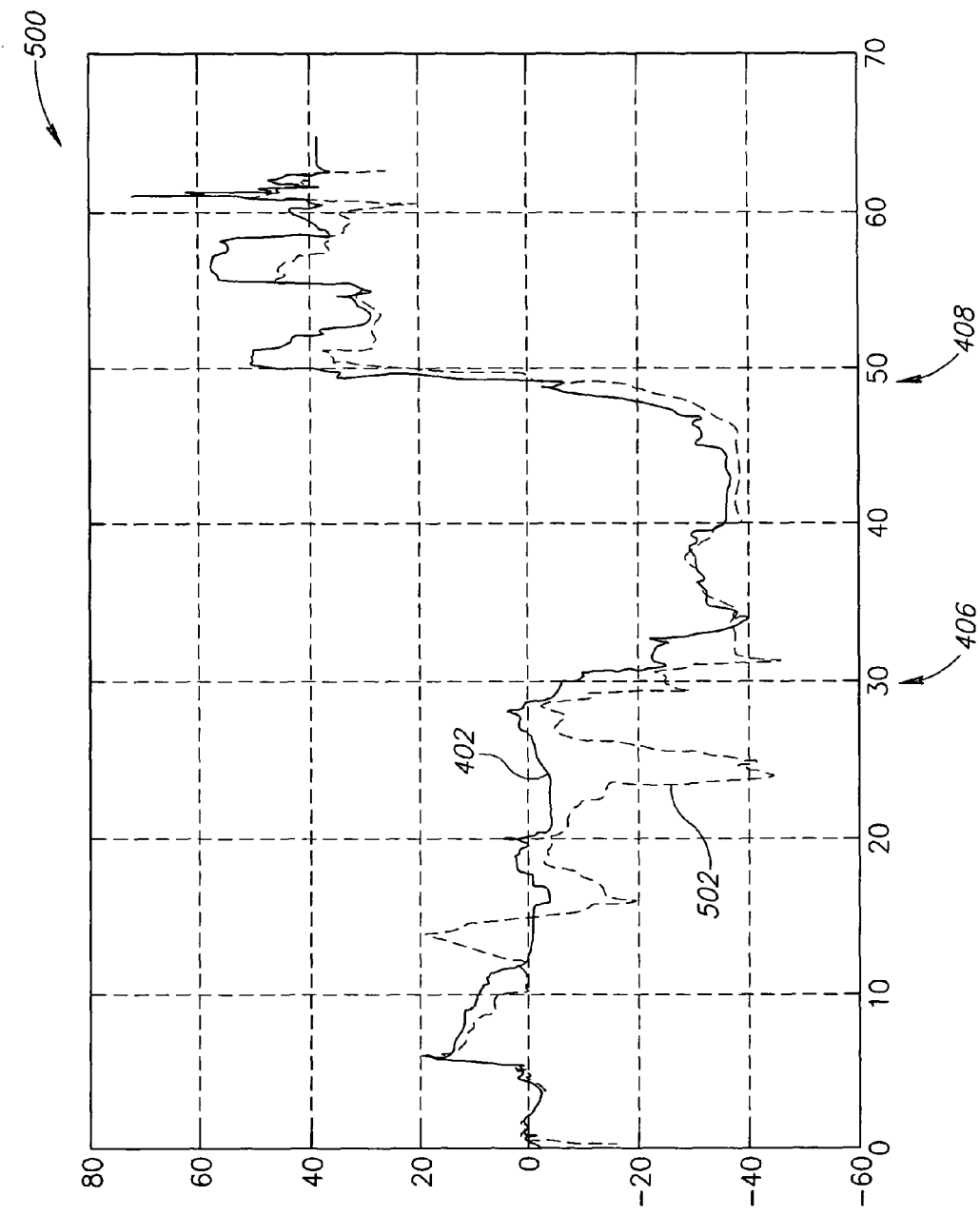
FIG. 5 schematically shows a graph of the cerebral blood flow indicator shown in FIG. 4, showing the effect of including all of the cardiac cycles, and including only the good cardiac cycles, according to an exemplary embodiment of the invention.

FIG. 5 shows a graph 500, illustrating the effect on the CBF indicator of discarding bad cardiac cycles. The CBF indicator signals shown in graph 500 were calculated from the same data used in FIG. 4. CBF indicator signal 402, shown as a solid line, was calculated using only "good" cardiac cycles, and is the same as signal 402 shown in FIG. 4. Good cardiac cycles were defined as those for which the duration of the cardiac cycle was less than 1.65 times the median duration of all cardiac cycles, and for which both the IPG and PPG signals had a cross-correlation of at least +0.7 between that cardiac cycle and the following cardiac cycle. CBF indicator signal 502, shown as a dashed line, was calculated in the same way, but including signal data from all cardiac cycles. Although signal 502 shows the same general trend as signal 402, decreasing while the arteries are clamped and returning to an even higher level after the arteries are released, signal 502 shows considerably more noise than signal 402.

Figure 6:
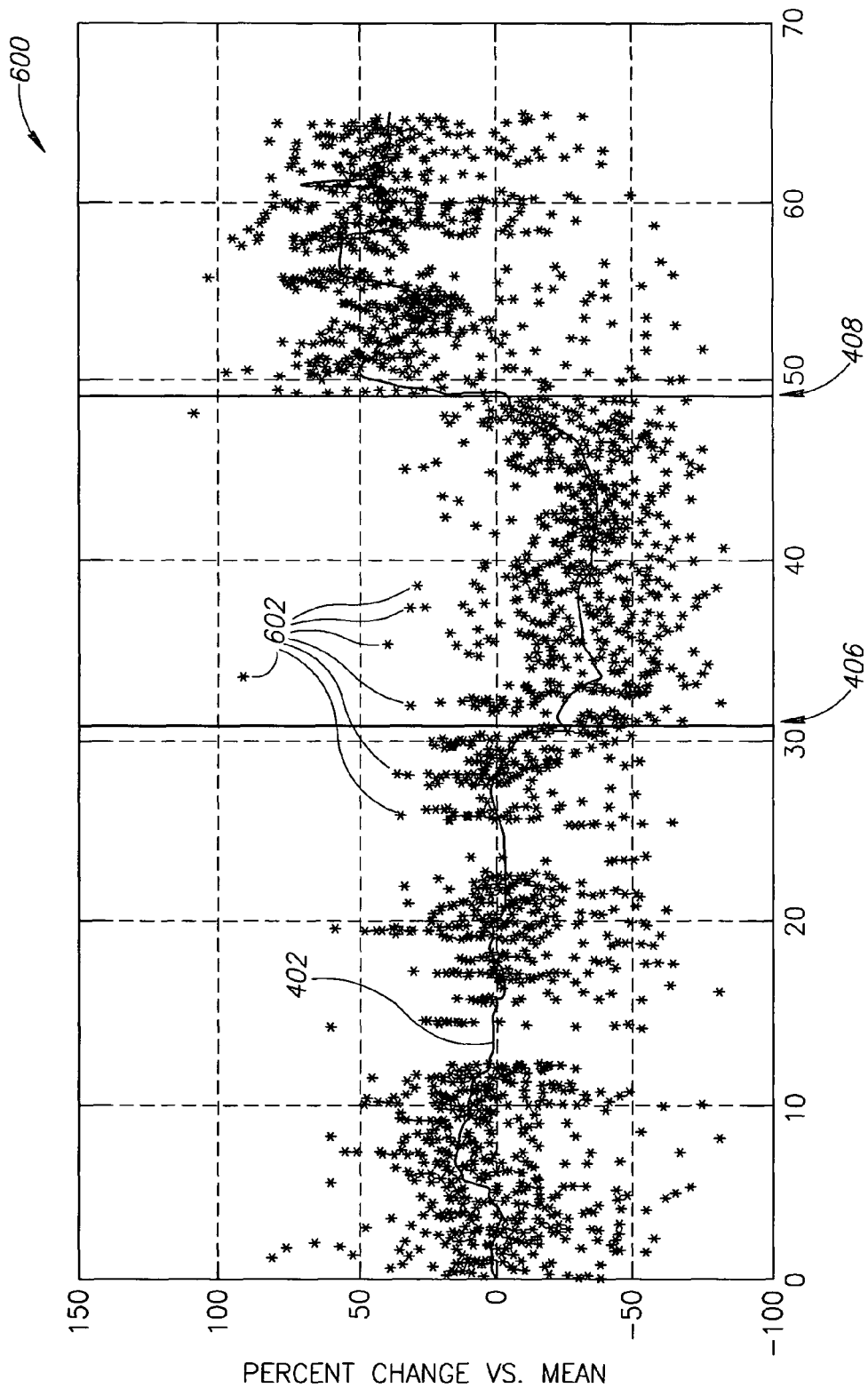
FIG. 6 schematically shows a graph of the cerebral blood flow indicator shown in FIG. 4, which was smoothed over time, together with the values of the indicator before smoothing, according to an exemplary embodiment of the invention.

FIG. 6 shows a graph 600, illustrating the effect of smoothing on the CBF indicator. Smoothed CBF indicator 402 plotted in graph 600 is the same as signal 402 plotted in FIGS. 4 and 5. A large number of small stars 602 show the values of the CBF indicator for individual cardiac cycles, which show a much higher level of noise than smoothed signal 402.

Figure 7:
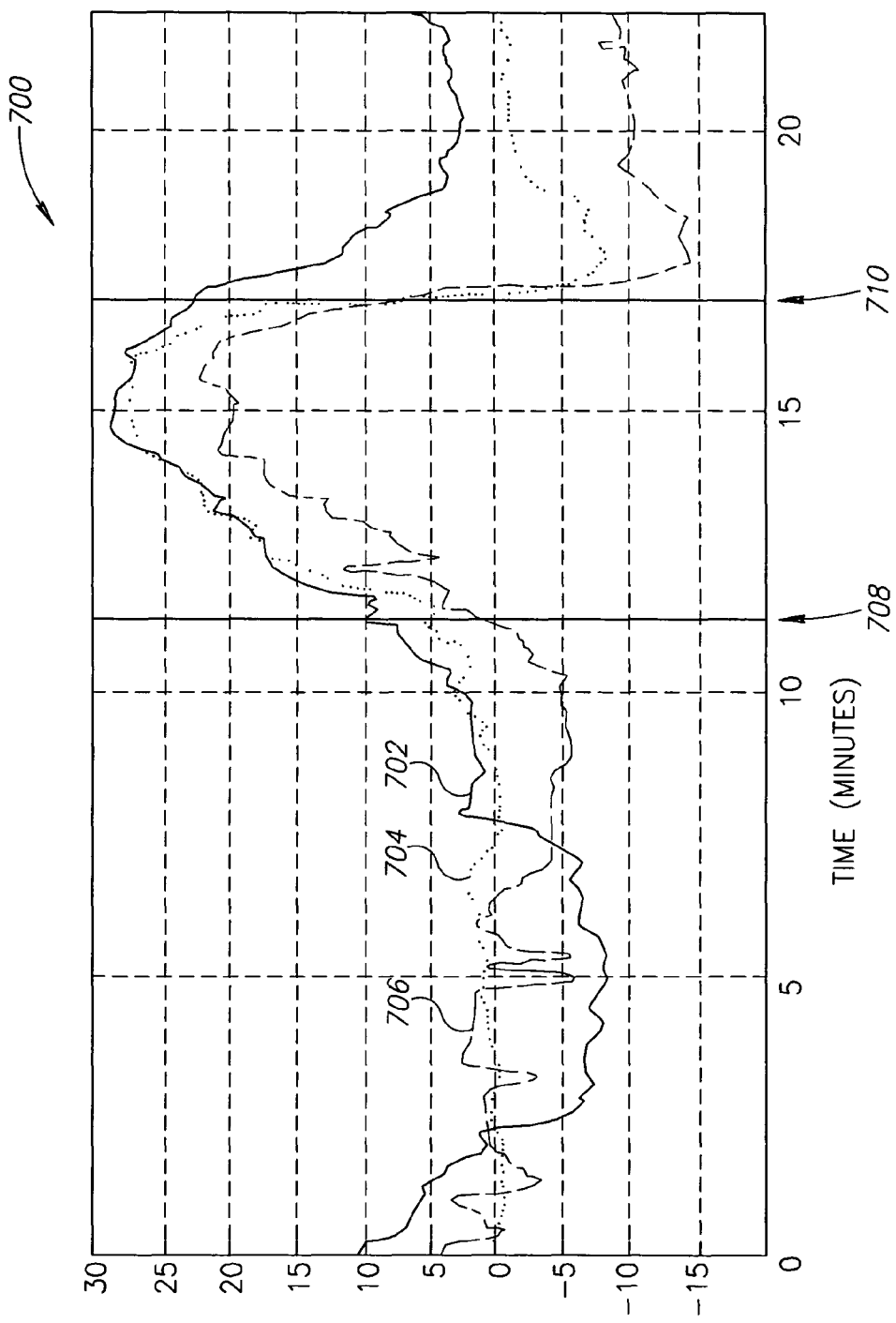
FIG. 7 schematically shows a graph of a calculated cerebral blood flow indicator of a subject as a function of time, according to an exemplary embodiment of the invention, during a test in which the cerebral blood flow was increased by having the subject breath air with an increased level of carbon dioxide.
Figure 8:
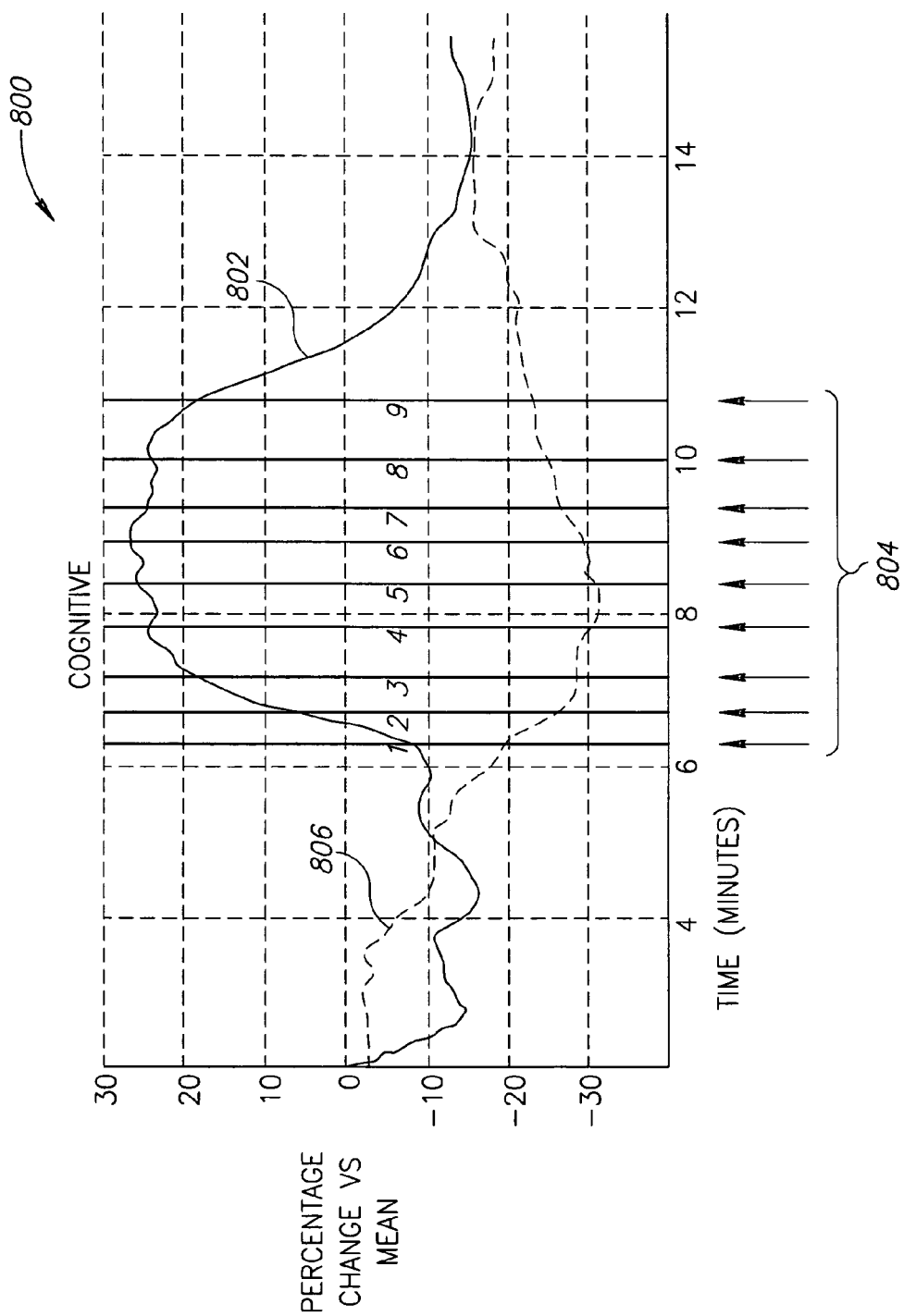
FIG. 8 schematically shows a graph of a calculated cerebral blood flow indicator for the left and right hemispheres of a subject's brain as a function of time, according to an exemplary embodiment of the invention, during a test in which the subject performed a cognitive task which increased the left hemisphere blood flow.

FIGS. 7 and 8 show the results of two other tests that were performed by the inventors to verify the usefulness of the CBF indicator signal, using healthy volunteers. In these tests, CBF indicators 702 (in FIG. 7) and 802 and 806 (in FIG. 8) were defined as the ratio of the maximum slope of the IPG signal to the maximum slope of one of the PPG signals, but the maximum slopes were not normalized to the amplitudes of the respective signals. This method of calculating the CBF indicator generally gave better results in these two tests, than using normalized maximum slopes did. The smoothing method, and the definition of "good" cardiac cycles, were the same as for CBF indicator 402 in FIGS. 4-6.

In the test used to generate the data plotted in graph 700 in FIG. 7, the subject breathed normal air until time 708. Between time 708 and time 710, the subject breathed from a closed bag, resulting in an increased level of carbon dioxide, a procedure which is known to provoke an increase in cerebral blood flow. After time 710, the subject returned to breathing normal air. The measured level of carbon dioxide in the gas that the subject exhaled, relative to a typical normal exhaled carbon dioxide partial pressure of 40 mm Hg, is plotted in graph 700 as signal 704. As expected, CBF indicator 702 rises when the level of carbon dioxide rises, and falls again when the level of carbon dioxide falls. The change in CBF indicator 702 is due largely to changes in the PPG signal, which decreases when the level of carbon dioxide increases, because the brain constricts peripheral arteries of the head, in order to assure a continued adequate supply of oxygen to the brain. A smoothed TCD signal 704, a standard indicator for cerebral blood flow, shows a similar rise when the level of carbon dioxide rises.

FIG. 8 illustrates the effect of cognitive activity on cerebral blood flow. CBF indicator 802 was calculated using the PPG signal from the left side of the head. CBF indicator 802 should indicate specifically the blood flow in the left side of the brain, since the brain is known to constrict or relax the peripheral arteries separately on either the left or the right side of the head, in order to regulate the blood flow on the corresponding sides of the brain. The subject was presented with nine multiplication problems, and asked to solve them in his head, at the times indicated by arrows 804. Mental arithmetic is known to be an activity primarily of the left side of the brain, and during the time the subject was solving the problems, CBF indicator 802 showed an increase in left cerebral blood flow, with about a two minute delay. By contrast, CBF indicator 806, which was calculated using the PPG signal from the right side of the head, shows no such increase, indicating that there was no increase in right cerebral blood flow during this period. CBF indicator 806 may even show a slight decrease during this period. The changes in both CBF indicators are due primarily to changes in the PPG signal.

Optionally, a device for performing the methods described herein may include a controller. A controller may include any of a power supply, analyzer, recording device, and monitor, and may control the currents sent to the current-carrying electrodes, and analyzing and processing the data. Optionally, the controller may include any of a CPU, power electronics, an AC/DC converter, and non-volatile memory to store software and data. Optionally, different elements of the controller may be located in different places, for example the power supply and the recording device, and/or the controller or parts of the controller may be packaged separately.

The invention has been described in the context of the best mode for carrying it out. It should be understood that not all features shown in the drawing or described in the associated text may be present in an actual device, in accordance with some embodiments of the invention. Furthermore, variations on the method and apparatus shown are included within the scope of the invention, which is limited only by the claims. Also, features of one embodiment may be provided in conjunction with features of a different embodiment of the invention. As used herein, the terms "have", "include" and "comprise" or their conjugates mean "including but not limited to." As used herein, the "slope" of a signal can mean either the unnormalized slope or the normalized slope, for example the slope normalized to a measure of the amplitude of the signal.

The invention claimed is:

1. An apparatus for estimating time-varying cerebral blood flow, the apparatus comprising:
   a controller configured to:
   obtain a time-varying impedance plethysmography signal from a head of a subject;
   use the impedance plethysmography signal to calculate a time-varying cerebral blood flow indicator; and
   perform data processing on the impedance plethysmography signal and the cerebral blood flow indicator to reduce at least one of noise and artifacts, wherein performing data processing comprises discarding cardiac cycle data of the impedance plethysmography signal for a cardiac cycle which meets one or more criteria for discarding, and
   wherein the criteria comprise the impedance plethysmography signal having a cross-correlation below a threshold, between the cardiac cycle and at least one of a following cardiac cycle and a preceding cardiac cycle.

2. An apparatus according to claim 1, wherein the criteria comprise having a duration of the cardiac cycle outside an expected range.

3. An apparatus according to claim 2, wherein the expected range has a maximum between 1.3 and 2 times an average duration of cardiac cycles.

4. An apparatus according to claim 1, wherein the at least one of a following cardiac cycle and a preceding cardiac cycle is a following cardiac cycle.

5. An apparatus according to claim 1, wherein the at least one of a following cardiac cycle and a preceding cardiac cycle is a preceding cardiac cycle.

6. An apparatus according to claim 1, wherein the criteria comprise impedance plethysmography signal having the cross-correlation below the threshold between +0.5 and +0.8, between the cardiac cycle and the at least one of a preceding and a following cardiac cycle.

7. An apparatus according to claim 1, wherein performing data processing comprises reducing breathing artifacts in the impedance plethysmography signal.

8. An apparatus according to claim 1, wherein performing data processing comprises smoothing the cerebral blood flow indicator.

9. An apparatus according to claim 8, wherein smoothing comprises finding an average over a time interval.

10. An apparatus according to claim 8, wherein smoothing comprises using a time scale that is adjusted adaptively, depending on behavior of the cerebral blood flow indicator as a function of time.

11. An apparatus according to claim 1, wherein the controller is further configured to determine a duration of the cardiac cycle using the impedance plethysmography signal.

12. An apparatus according to claim 1, wherein the cerebral blood flow indicator is the peak-to-peak amplitude of the impedance plethysmography signal over the cardiac cycle.

13. An apparatus according to claim 1, wherein the cerebral blood flow indicator is an average value of the impedance plethysmography signal over the cardiac cycle.

14. An apparatus according to claim 1, wherein the cerebral blood flow indicator is a maximum slope of the impedance plethysmography signal over the cardiac cycle.

15. An apparatus according to claim 1, wherein performing data processing includes adjusting the impedance plethysmography signal to have a substantially constant minimum value for a plurality of cardiac cycles.

16. An apparatus according to claim 1, wherein the controller is further configured to calculate the time varying cerebral blood flow indicator for a left hemisphere and a right hemisphere of a brain of the subject.

17. An apparatus for estimating time-varying cerebral blood flow, the apparatus comprising:
a controller configured to:
obtain a time-varying impedance plethysmography signal from a head of a subject;
use the impedance plethysmography signal to calculate a time-varying cerebral blood flow indicator; and
perform data processing on the impedance plethysmography signal and the cerebral blood flow indicator to reduce at least one of noise and artifacts,
wherein performing data processing comprises smoothing the cerebral blood flow indicator, and
wherein smoothing comprises using a time scale that is adjusted adaptively, depending on behavior of the cerebral blood flow indicator as a function of time.

18. An apparatus for estimating time-varying cerebral blood flow, the apparatus comprising:
a controller configured to:
obtain a time-varying impedance plethysmography signal from a head of a subject;
use the impedance plethysmography signal to calculate a time-varying cerebral blood flow indicator; and
perform data processing on the impedance plethysmography signal and the cerebral blood flow indicator to reduce at least one of noise and artifacts,
wherein the cerebral blood flow indicator is the peak-to-peak amplitude of the impedance plethysmography signal over a cardiac cycle.

19. An apparatus for estimating time-varying cerebral blood flow, the apparatus comprising:
a controller configured to:
obtain a time-varying impedance plethysmography signal from a head of a subject;
use the impedance plethysmography signal to calculate a time-varying cerebral blood flow indicator; and
perform data processing on the impedance plethysmography signal and the cerebral blood flow indicator to reduce at least one of noise and artifacts,
wherein performing data processing includes adjusting the impedance plethysmography signal to have a substantially constant minimum value for a plurality of cardiac cycles.

20. An apparatus for estimating time-varying cerebral blood flow, the apparatus comprising:
a controller configured to:
obtain a time-varying impedance plethysmography signal from a head of a subject;
use the impedance plethysmography signal to calculate a time-varying cerebral blood flow indicator; and
perform data processing on the impedance plethysmography signal and the cerebral blood flow indicator to reduce at least one of noise and artifacts, and
wherein the controller is further configured to calculate the time varying cerebral blood flow indicator for a left hemisphere and a right hemisphere of a brain of the subject.

* * * * *